United States Patent [19]
Lackey et al.

[11] Patent Number: 5,702,464
[45] Date of Patent: Dec. 30, 1997

[54] MODULAR TRIAL TIBIAL INSERT

[75] Inventors: Jennifer J. Lackey; Albert J. Pothier; Thomas A. Carls; Chris E. Johnson; Scott Elliott, all of Memphis, Tenn.

[73] Assignee: Smith & Nephew Inc., Memphis, Tenn.

[21] Appl. No.: 603,581

[22] Filed: Feb. 20, 1996

[51] Int. Cl.⁶ .................... A61F 2/30; A61F 2/38
[52] U.S. Cl. .......................... 623/20; 623/18
[58] Field of Search ......................... 623/20, 18

[56] References Cited

U.S. PATENT DOCUMENTS

| | | | |
|---|---|---|---|
| 4,207,627 | 6/1980 | Cloutier | 3/1.911 |
| 4,211,228 | 7/1980 | Cloutier | 128/303 R |
| 4,257,129 | 3/1981 | Volz | 3/1.911 |
| 4,731,086 | 3/1988 | Whiteside et al. | 623/20 |
| 4,769,039 | 9/1988 | Horber | 623/20 |
| 4,808,185 | 2/1989 | Penenberg et al. | 623/20 |
| 4,842,606 | 6/1989 | Kranz et al. | 623/23 |
| 4,911,987 | 3/1990 | Sakata et al. | 428/469 |
| 4,936,847 | 6/1990 | Manginelli | 623/23 |
| 4,944,757 | 7/1990 | Martinez et al. | 623/20 |
| 4,950,298 | 8/1990 | Gustilo et al. | 623/20 |
| 5,019,103 | 5/1991 | Van Zile et al. | 623/20 |
| 5,047,058 | 9/1991 | Roberts et al. | 623/20 |
| 5,108,442 | 4/1992 | Smith | 623/20 |
| 5,108,452 | 4/1992 | Fallin | 623/23 |
| 5,152,797 | 10/1992 | Luckman et al. | 623/20 |
| 5,201,769 | 4/1993 | Schutzer | 623/23 |
| 5,282,868 | 2/1994 | Bahler | 623/20 |
| 5,405,396 | 4/1995 | Heldreth et al. | 623/20 |
| 5,458,637 | 10/1995 | Hayes | 623/16 |

FOREIGN PATENT DOCUMENTS 2 259 253A 3/1993 United Kingdom.

OTHER PUBLICATIONS

Osteonics Modular Tibial Trial Inserts Brochure, Trial Reduction, p. 8, Figure 8.

*Primary Examiner*—Michael J. Milano
*Assistant Examiner*—Tram Anh T. Nguyen
*Attorney, Agent, or Firm*—Pravel, Hewitt, Kimball & Krieger

[57] ABSTRACT

A modular tibial trial prosthesis for attachment to a patient's surgically cut proximal tibia includes a tibial tray having proximal and distal surfaces, the distal surface to be fitted against the patient's surgically prepared proximal tibia during knee joint replacement surgery. The proximal surface of the tray accepts any one of a plurality of plastic liner inserts that fits the tray at the proximal tray surface with an interlocking connection. The liner inserts each have a distal surface for attachment to the tray and a proximal articulating surface that is receptive of a distal femoral articulating surface. The proximal articulating surface has concavely-shaped portions. The concavely-shaped portions of the liner inserts provide different articular geometries for selection by the user. A plurality of spacers of different thicknesses can be positioned in between a selected one of the plastic liner inserts and the tibial tray. Each spacer has proximal and distal surfaces. The spacers have connecting portions on each of said proximal and distal surfaces for forming respective connections with a tibial tray and a selected plastic liner insert. The liner inserts each have connecting portion on the distal surface thereof for connecting to the proximal surface of the spacer and to the proximal surface of the tray. The liner inserts and spacers each have a periphery in the form of a sidewall that extends generally perpendicular to the proximal surface of the patient's transversely cut proximal tibia. The periphery of the insert and spacers are of corresponding shape.

31 Claims, 4 Drawing Sheets

| Articular Geometry | Thickness | | | | | | | |
|---|---|---|---|---|---|---|---|---|
| | 9 mm | 11 mm | 13 mm | 15 mm | 18 mm | 21 mm | 25 mm | 30 mm |
| Cruciate Retaining | x | x | x | x | x | | | |
| Deep Dished | x | x | x | x | x | x | | |
| Posterior stabilized | x | x | x | x | x | x | x | |
| Constrained | | x | x | x | x | x | x | x |

| | Color |
|---|---|
| Cruciate Retaining 9 mm insert trial is modular (will accept a spacer) | Blue |
| Cruciate Retaining 11 mm insert trial is non-modular (will not accept a spacer) | Blue |
| Deep Dished 9 mm insert trial is modular (will accept a spacer) and has one socket | Red |
| Deep Dished 11 mm insert trial is non-modular (will not accept a spacer) | Red |
| Posterior Stabilized 9 mm insert trial is modular (will accept a spacer) and has two sockets | Yellow |
| Posterior Stabilized 11 mm insert trial is non-modular (will not accept a spacer) | Yellow |
| Constrained 9 mm insert trial is modular (will accept a spacer) and has three sockets and one peg | Green |
| Constrained 11 mm insert trial is non-modular (will not accept a spacer) | Green |
| 13 mm Spacer has one socket | Black |
| 15 mm Spacer has one socket | Grey |
| 18 mm Spacer has one socket | Blue |
| 21 mm Spacer has one socket and one peg | Red |
| 25 mm Spacer has one socket and two pegs | Yellow |
| 30 mm Spacer has one socket and three pegs | Green |

MODULAR TRIAL TIBIAL INSERT

SPECIFICATION

BACKGROUND OF THE INVENTION:

1. Field of the Invention

The present invention relates to orthopedic surgical trial implants, and more particularly to an improved tibial trial prosthesis in the form of a kit that includes modular trial tibial inserts that offer a series of articular topographies that can be combined with a series of spacers to make up a range of inserts available to a surgeon in a total knee replacement instrumentation set.

2. General Background

During total knee replacement surgery, the surgeon prepares the patient's proximal tibia to receive a tibial implant. The surgeon also prepares the distal femur of the patient with surgical cuts so that it can receive a femoral component.

It is often desirable to first attach the femoral component to the patient's distal femur before placing the tibial prosthesis component. One of the reasons for placing the tibial component after the femoral component is that the tibial prosthesis uses a polymeric liner for articulating with a smooth polished metallic surface on the femoral component. Thus, the liner affords a removable adjustable member that can be switched by the surgeon to achieve a good fit.

A tibial prosthesis component includes a metallic tray typically having a stem that fits the patient's proximal tibia at the intramedullary canal. This tray typically provides connecting portions for forming a connection with a polymeric liner. One of the more common connections of a liner to a tibial tray is a dovetail-type connection. Such dovetail arrangements are commercially available. Some have been patented.

Before placing the actual final tibial trial prosthesis, the surgeon can use a number of different trial prostheses in a search for the best fit. The surgeon can thus use trial prosthesis trays of different size and configuration as well as different polymeric liner inserts.

Another problem with the use of a trial prosthesis to obtain a good fit is that of differences in articular topographies. It would be desirable to offer a series of articular topographies for the plurality of liners to the trial prosthesis. However, the articular geometries are expensive to manufacture and they call for differences in overall thickness. Therefore, to have a separate insert or liner with every possible overall articular geometry and with every possible thickness is very expensive.

There are presently commercially available trial prosthesis kits that are one-piece parts. DePuy has made a few of their thicker P/S inserts modular by using a dovetail medial/lateral sliding locking mechanism.

Various patents have been issued that relate to tibial prostheses, some using dovetail connections between the liner insert and the tray. An example of a patent for a knee prosthesis is U.S. Pat. No. 4,207,627 issued to Cloutier. The Cloutier device relates to an improved total knee prosthesis of the non-hinged type which advantageously provides normal knee motion and stability during ambulation while substantially obviating loosening or cold flowing of the tibial component. For this purpose, the total knee prosthesis substantially adopts the anatomical configuration of the natural knee and includes a tibial component comprising condylar bearing members with lower portions completely embedded in tray-shaped elongated sections, in which they are mounted with a predetermined clearance to mechanically absorb part of the natural stresses and torques. The condylar bearing members are also removable and replaceable to obviate any misalignment, natural or not.

The Cloutier U.S. Pat. No. 4,211,228 discloses a multi-purpose template comprising a Y-shaped element comprising a flat handle integrally extended at one end by two flat, which elongated prongs are symmetrically arranged with respect to a vertical plane passing through the axis of the Y-shaped element perpendicularly to the general plane thereof; an alignment rod fixable onto the flat handle near its integrally extended end, which is substantially perpendicular to the general plane of the Y-shaped element; and a set of provisional plateaus of different thicknesses for each prong, for determining the thickness of condylar bearing members to be used in the total knee prosthesis. This template is particularly useful in total knee arthroplasty for determining the desired location of the tibial prosthesis component on the patient's tibia, the width or the amount of tibial eminence to be preserved, the planes of tibial plateau osteotomies, the location of the fixation studs of the tibial prosthesis component and the appropriate thickness of the tibial prosthesis component to be used, as well as for testing the range of motion of the knee prior to installing the tibial component and testing the latter as such prior to fixing it on the patient's tibia.

A tibial prosthesis, template and reamer are disclosed in U.S. Pat. No. 4,808,185 issued to Penenberg et al. The improved tibial prosthesis and a template and reamer are utilized in installing the prosthesis on the proximal end of a surgically prepared tibia. The prosthesis comprises a tibial component including a tray attached to the proximal tibia and an insert attached to the tray and provided to present an articulating surface for bearing engagement with the distal end of the femur or alternatively with a femoral component which has been surgically attached to the distal end of the femur. The tray includes an exterior surface including a plurality of domical contours which interengage with corresponding surfaces formed in the proximal tibia by the surgeon. The tray is preferably attached to the proximal tibia through the use of screw fasteners extending through openings formed in the domical contours. The template is utilized by the surgeon in measuring the exact location and size of the contours which are to be surgically formed in the proximal tibia. The reamer is specifically designed to enable its use during the surgical procedure to surgically create the contours which are formed in the proximal tibia.

A locking assembly for a prosthetic implant is disclosed in U.S. Pat. No. 5,108,442, entitled "Prosthetic Implanting Locking Assembly", issued to Todd Smith. The assembly comprises a base component secured to a bone and a generally planar surface having a recessed portion formed therein. A spring is situated in the recessed portion of the base component and includes a tab extending away from the spring. A bearing component slidably engages the base component to couple the bearing component to the base component and the bearing is provided with an opening for receiving the tab of the spring means therein to lock the bearing component in a fixed position relative to the base component. The base component is shown as including a stem. A dovetail-like locking mechanism is shown interfacing the tibial base and the polymeric liner.

U.S. Pat. No. 4,257,129, issued to Volz and entitled "Prosthetic Knee Joint Tibial", discloses a prosthetic implant for replacement of the proximal end of the tibia. This implant includes a metal anchor member which is cemented into the intramedullary canal of the tibia and a replaceable high density polyethylene articulation member which is pinned to the anchoring member. The anchoring member and the replaceable articulation member slidably fit together by movement in a lateral direction by means of a dovetail fitting and a raised tab portion is provided as a stop means in order to assure proper positioning of one member with respect to the other. Once the two members are properly aligned, a vertical pin is inserted therethrough and is secured in position by a two prong horizontal clip arrangement which inserts through the articulation member and clips about a reduced diameter portion of the vertical pin member. Notches are provided in both the anchoring member as well as the replaceable articulation member for clearance of ligaments and the outer peripheral edge of the anchoring member includes a depending sharp lip and a depending groove therebehind which facilitate cementing of the anchoring member in place by compacting acrylic bone cement into the prepared surface of the tibia.

A prosthetic arrangement for a complex joint such as a knee joint is disclosed in the Bahler U.S. Pat. No. 5,282,868. To permit movement of coupling elements which carry joint surfaces congruent with condylar portions of the prosthesis, the coupling elements are slidable in guide tracks which are curved and are widened at their terminal portions. The coupling elements have elongated engagement ribs which fit into a guide track groove, with minimum clearance and play at the narrowest central portion of the guide groove while permitting limited twisting as well as sliding movement due to the widened regions of the guide track at its end region. The position of the guide track rib can be reversed, if desired. The elements slide on a slide surface and can be retained, for example, by an interlocking connection such as a dovetail.

A modular tibial prosthesis is the subject of U.S. Pat. No. 5,405,396, issued to Heldreth et al. The prosthesis contains a dovetail mechanism and a posterior tongue and groove arrangement. The dovetail mechanism cooperates with a reinforcing component to allow alternate use of a spline component with the same base plate.

An orthopedic base component and augmentation block is disclosed in U.S. Pat. No. 5,458,637 issued to Hayes. The orthopedic base component and augmentation block, such as a provisional tibial component, includes an attachment mechanism that ensures that the augmentation block cannot inadvertently shift about or disconnect from the tray component. The attachment mechanism uses a button and "key hole" shaped opening to attach the augmentation block to the tray component. The "key hole" opening is formed in the distal surface of the tray component. The "key hole" configuration is formed by an elongated slot and a circular bore. Two oppositely facing protuberances extend into the posterior end of each slot from the peripheral side wall which define the slot. The button extends transversely from the proximal surface of the augmentation block and includes a substantially rectangular neck and a flat circular head. A neck has an indentation formed on two opposed sides and the button is securely held at the posterior end of the slot by protuberances which are restrictively seated within the neck.

Other patents that disclose various modular augment-type members which are attached in various ways to a base implant component include U.S. Pat. Nos. 5,201,769; 5,152,797, 5,108,452; 5,047,058; 5,019,103; 4,950,298; 4,944,757; 4,936,847; 4,911,987; 4,842,606; 4,769,039; 4,731,086; and U.K. Patent Application GB 2 259 253A. The Fallin Patent 5,108,452 discloses an augment in FIGS. 18–25 which include a wedge locking member that fits into a socket and provides a wedge lock connection via mating inclined locking surfaces.

An Osteonics commercially available trial prosthesis is known as the Series 7000 Tibial Bearing Trials. These trials are said to be modular in design. Commercial literature states that to prepare the trial for the primary posteriorly stabilized knee, the user chooses the appropriate sized Series II Tibial Bearing Trial and P/S I Tibial Trial Cap. These items are set to be color coordinated by size. The user snaps the trial cap into the bearing trial. The assembled trial may now be attached to the tibial base plate.

SUMMARY OF THE INVENTION

The present invention Solves prior art problems and shortcomings by offering a series of articular topographies that can be combined with a series of spacers that make up a range of inserts available in a total knee set. Thus, a plurality of different articular geometries can be provided in the thinner, most commonly used available sizes. Spacers can then be combined with a desired articular geometry liner insert to obtain a desired thickness.

A spacer of a given thickness can thus be combined with any one of a plurality of liners having respective different articular geometries. Therefore, if the different articular geometries are manufactured in the thinnest available sizers, spacers can be attached to these different articular surfaces in order to reduce the overall cost of the trials to the end users.

The present inventions provides a modular trial tibial insert system that includes polymeric inserts that can be assembled using a top portion having a desired articular geometry (for example, cruciate retaining, deep dished, posterior stabilized, constraining, etc.) This top member with the particular articular geometry can be thickened by adding a spacer between the articular insert member and the tibial tray.

By offering a series of articular topographies for the top portions of the liner that can be combined with a series of spacers making up the range of inserts available in the total knee set, the number of trials and the space needed in sterilization trays would be reduced substantially.

With the present invention, the top members of each liner having the articular geometry are manufactured according to the present invention in the thinnest available sizes. Spacers are then used to thicken the liners if desired. The spacers can be attached to any of the different articular surfaces provided with the top portions of each liner insert.

The trial articular inserts of the present invention can thus be provided in different thicknesses by using spacers or shims that increase the thickness of the liner insert. The shim or spacer is placed in between the tibial trial tray and the trial articular insert. As an example, if a 10 mm thickness insert is too loose, a surgeon can slide a 2 mm shim or spacer under it and it now becomes a 12 mm liner insert comprised of two plastic or polymeric members—the insert liner and the spacer.

The present invention provides an improved tibial trial prosthesis that includes a tibial tray having a proximal and a distal surface. The distal surface is fitted against the patient's surgically prepared proximal tibia during knee joint replacement surgery.

A plastic liner fits the tray with an inner locking connection. The liner has a distal surface and a proximal articulating surface that is receptive of a distal femoral articulating surface. The proximal articulating surface has concavely-shaped articulating portions.

A plurality of spacers are provided of different thicknesses. A selected one of the spacers can be positioned in between the plastic liner and the tibial tray. Each spacer has a proximal and distal surfaces. At least one of the spacers has connecting portions on each of its proximal and distal surfaces for forming respective connections with the tibial tray and the plastic liner insert.

The liner insert has a connecting portion on its distal surface for connecting to either the proximal surface of the spacer or to the proximal surface of the tray if a spacer is not being used.

The liner inserts and spacers each have a periphery in the form of a sidewall. These peripheral sidewalls are of corresponding shape and produce a common sidewall upon assembly at least over a majority of the distance about the periphery of the assembled insert and spacer. The common sidewall can function generally as an extension of the periphery of the surgically cut proximal tibia. However, the insert sidewall can be smaller than the periphery of the tibial tray or cut proximal tibia.

The proximal articulating surface of each liner insert can be a cruciate retaining articular geometry, a deep dish articular geometry, a posterior stabilized articular geometry, or a constraining articular geometry.

There are a plurality of spacers of different thicknesses as measured between the proximal and distal surfaces of each spacer. Thus, the trial prosthesis is comprised of an assembly of a tray, a spacer, and a liner, or of an assembly of a tray and a liner.

In the preferred embodiment, a kit is provided that is modular for assembling a desired trial tibial insert liner during knee joint replacement surgery. There can be a plurality of trial trays and a plurality of spacers of differing thicknesses that attach to each tray. Each spacer thickness is measured between the proximal and distal surfaces of a selected spacer. At least one of the trial prosthesis is comprised of an assembly of a selected tray and a selected liner. At least some of the trial prosthesis for a given trial tray size are comprised of an assembly of a selected trial tray, a selected liner, and a selected spacer. There are at least some of the spacers that are thicker than the liner when measured between the proximal and distal surfaces of the liner.

The present invention thus provides a modular trial insert that can be assembled from a total knee set having a plurality of trays, a plurality of spacers, and a plurality of liners having articular geometry thereon. The present invention thus provides a modular tibial trial prosthesis for attachment to a patient's transversely cut proximal tibia. The apparatus includes a tibial tray having proximal and distal surfaces, the distal surface to be fitted against the patient's transversely cut proximal tibia during knee joint replacement surgery.

A plurality of plastic liner inserts fits the trial tray with an interlocking connection. The liner inserts each have a distal surface and a proximal articulating surface that is receptive of a distal femoral articulating surface. The proximal articulating surface has concavely-shaped portions with a desired geometry. The concavely-shaped portions of the liner inserts preferably provide a plurality of different articular geometries for selection by the user, such as, for example, cruciate retaining, deep dished, posterior stabilized, constraining, or the like.

A plurality of spacers can be positioned in between a selected one of the plastic liner inserts and the tibial tray. Each spacer has proximal and distal surfaces. The spacers have connecting portions on each of said proximal and distal surfaces for forming respective connections with a tibial tray and a selected plastic liner insert.

The liner inserts each have a connecting portion on the distal surface thereof for connecting to the proximal surface of the spacer and to the proximal surface of the tray.

The liner inserts and spacers each have a periphery in the form of a sidewall that extends generally perpendicular to the proximal surface of the patient's transversely cut proximal tibia. The combined periphery of the insert and its spacer is of corresponding shape to define a common sidewall that forms an extension generally to the periphery of the patient's proximal tibia. This common sidewall can correspond generally in shape to that of the proximal tibia at the transverse surgical cut. However, the insert sidewall can be smaller than the periphery of the tibial tray or cut proximal tibia.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein.

DETAILED DESCRIPTION OF THE PREFERRED EMBODIMENT

Figures 1, 2:
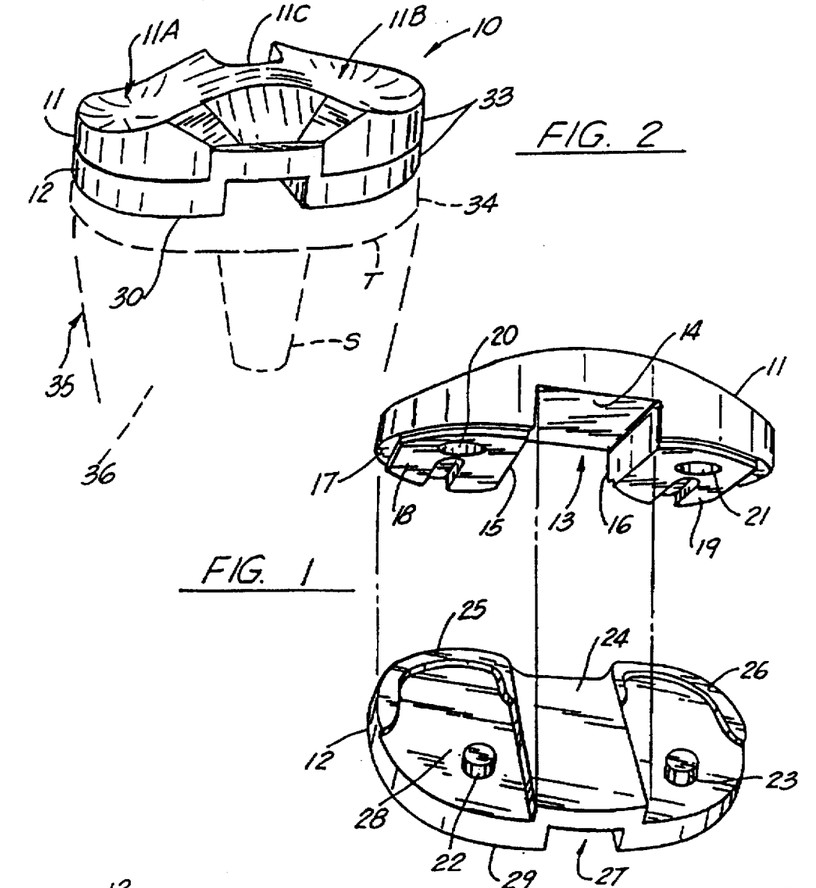
FIG. 1 is a perspective exploded view of the preferred embodiment of the apparatus of the present invention.
FIG. 2 is a perspective view of the preferred embodiment of the apparatus of the present invention.

FIGS. 1-4 show generally the preferred embodiment of the apparatus of the present invention designated generally by the numeral 10. In FIGS. 1 and 2, tibial trial insert 10 is comprised of a top member 11 having an articular surface that is comprised of concavities 11A and 11B, and raised portion 11C. The top member 11 of insert 10 can form an attachment to any one of a plurality of spacers 12 that would be provided in differing thicknesses. Thus, for example, if the top member 11 had a thickness of about 10 mm, a 2 mm spacer 12 could be added to give an overall thickness of 12 mm.

Figure 3:
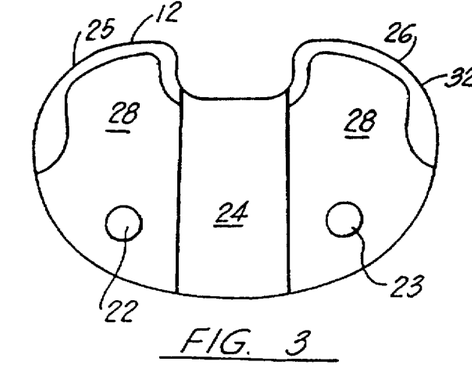
FIG. 3 is a proximal view of a spacer portion of the preferred embodiment of the apparatus of the present invention.
Figure 4:
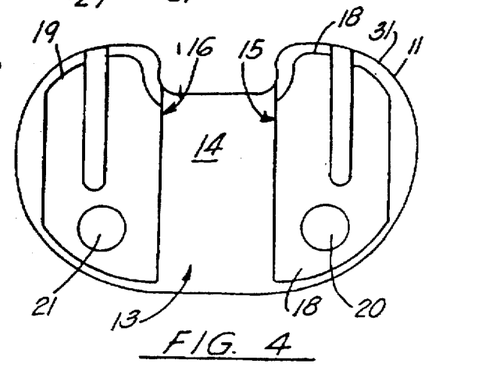
FIG. 4 is a view of the distal surface of a liner insert that is used with the apparatus of the present invention.

The combination of the top member 11 and spacer 12 defines a tibial trial insert 10 that can be custom sized and then fitted to a metallic tray T having a metallic stem S. In FIGS. 1, 3, and 4, the top member 11 provides a rectangular slot 13 defined by flat surfaces 14, 15, 16.

The distal surface 17 of top member 11 provides a pair of locking portions 18, 19 that form connections with correspondingly-shaped locking portions 25, 26 of spacer 12. A pair of openings 20, 21 are sized and shaped to fit to and conform to posts 22, 23 of spacer 12. Raised center portion 24 of spacer 12 fits and conforms to the flat surfaces 14, 15, 16 of slot 13. Rectangular slot 27 of spacer 12 fits a correspondingly-shaped rectangular projection on the proximal surface 30 of tray T. Proximal surface 28 of spacer 12 receives the distal Surface 17 of top member 11.

As shown in FIGS. 3 and 4, the top insert portion 11 and spacer 12 have correspondingly-shaped peripheral surfaces 31 and 32. These peripheral surfaces 31, 32 form a common wall 33 upon assembly, as shown in FIG. 2.

Figures 5, 6, 7, 8:
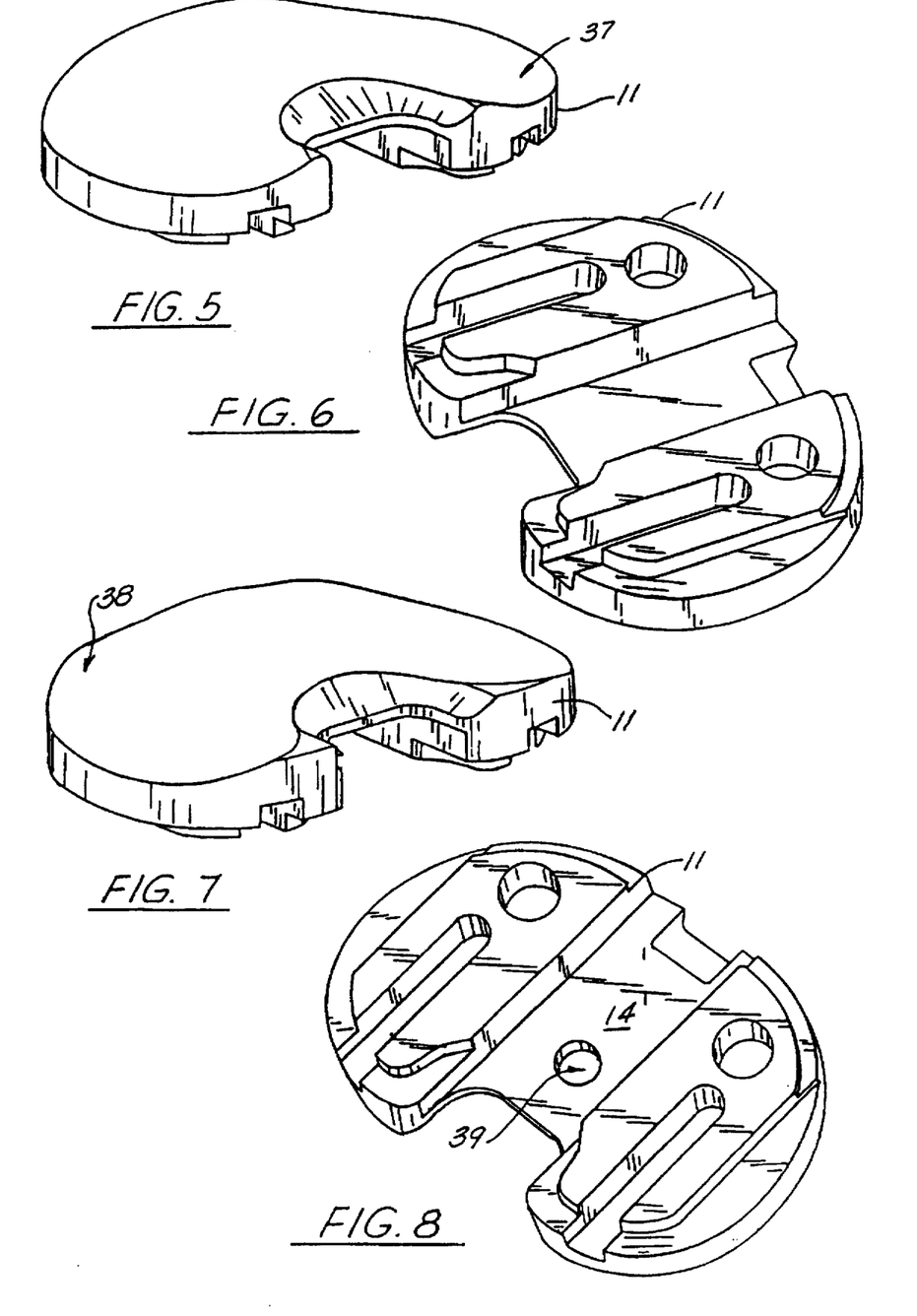
FIG. 5 is a perspective view of a trial insert liner portion of the preferred embodiment of the apparatus of the present invention illustrating a cruciate retaining articular geometry.
FIG. 6 is a distal perspective view of a cruciate retaining trial insert liner portion of the preferred embodiment of the apparatus of the present invention.
FIG. 7 is a proximal perspective view of a tibial trial insert portion of the preferred embodiment of the apparatus of the present invention illustrating a deep dished articular geometry.
FIG. 8 is a distal perspective view of the deep dished trial insert of FIG. 7.

In FIGS. 5–6, liner insert upper member 11 is shown having an articular geometry designated as articulating surface 37. For the member shown in FIGS. 5 and 6, the upper member 11 can form a connection with any spacer 12 that has no projecting portions as shown in FIGS. 1 and 3.

Figure 9:
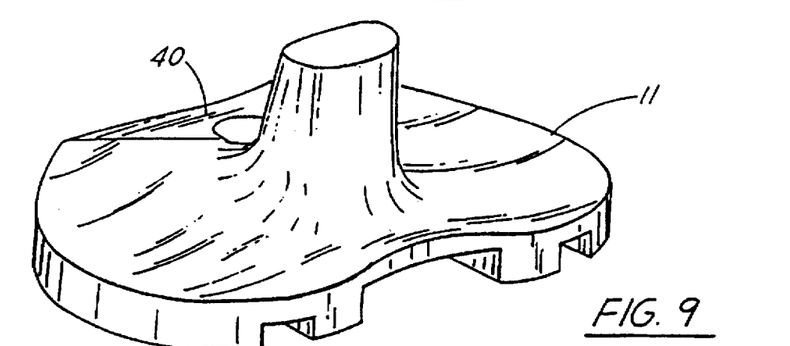
FIG. 9 is a proximal perspective view of the tibial trial insert liner portion of the preferred embodiment of the apparatus of the present invention illustrating a posterior stabilized articular geometry.
Figure 10:
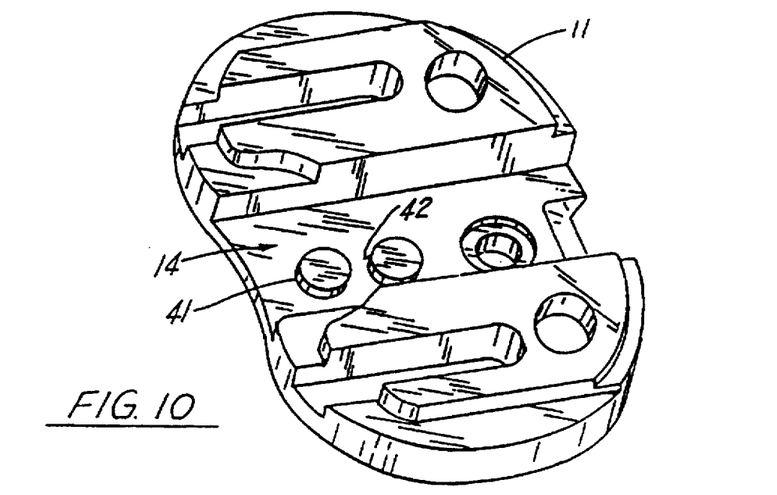
FIG. 10 is a bottom perspective view of the trial liner insert portion of the insert shown in FIG. 9.
Figure 11:
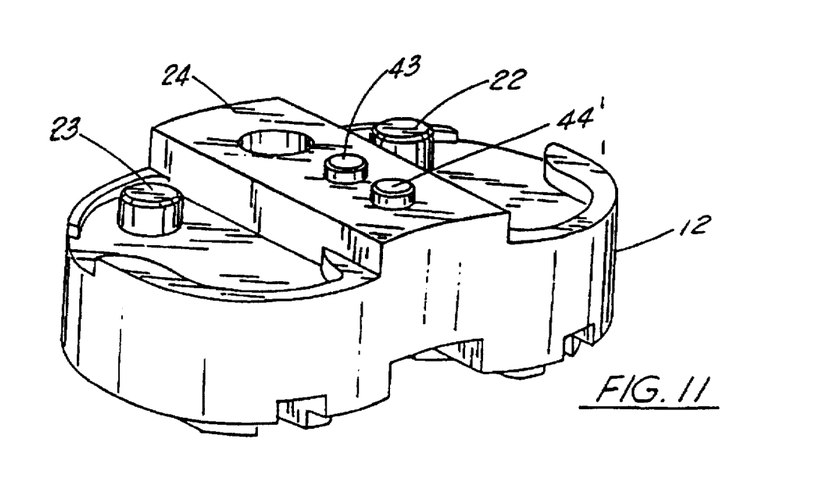
FIG. 11 is a perspective view of a spacer portion of the preferred embodiment of the apparatus of the present invention.

In FIGS. 7 and 8, a top member trial insert 11 is shown having an articulating surface that is a deep dished articular geometry. In FIG. 8, a cylindrically-shaped socket 39 is positioned at flat surface 14. For the member shown in FIGS. 7 and 8, the upper member 11 can form a connection with any spacer 12 that has one projecting portion from raised center portion 24. However, the top member 11 of FIGS. 7 and 8 will not fit a thicker liner such as the liner shown in FIG. 11 because it has a pair of projecting portions 43, 44. Thus, in order to form a connection between the spacer 12 of FIG. 11 and a top member 11, the top member 11 must necessarily provide more than one cylindrically-shaped socket. 39. For example, the posterior stabilized top member 11 of FIGS. 9 and 10 does provide a pair of cylindrically-shaped sockets 41, 42 at the surface 14. The top member 11 of FIGS. 9 and 10 will thus fit the spacer 12 of FIG. 11. The distal surface 14 of top member 11 shown in FIGS. 7 and 8 provides only one cylindrically-shaped opening 39. This ensures that the top member 11 shown in FIGS. 7 and 8 will not be stacked upon spacer 12 shown in FIG. 11 that has multiple projecting portions 43, 44.

The above described cylindrically-shaped sockets 39, 41, and 42 are examples. Other types of sockets could be provided on the top members 11 with correspondingly-shaped projections 43, 44 on the spacers 12. The use of such cylindrically-shaped sockets 39, 41, 42 and projecting portions such as 43, 44 allows the manufacturer to dictate to which top members 11 a spacer 12 can be attached. Thus, for example, the manufacturer may not want certain larger thickness spacers to be combined with a particular top member 11 having a particular articular geometry.

Figure 12:
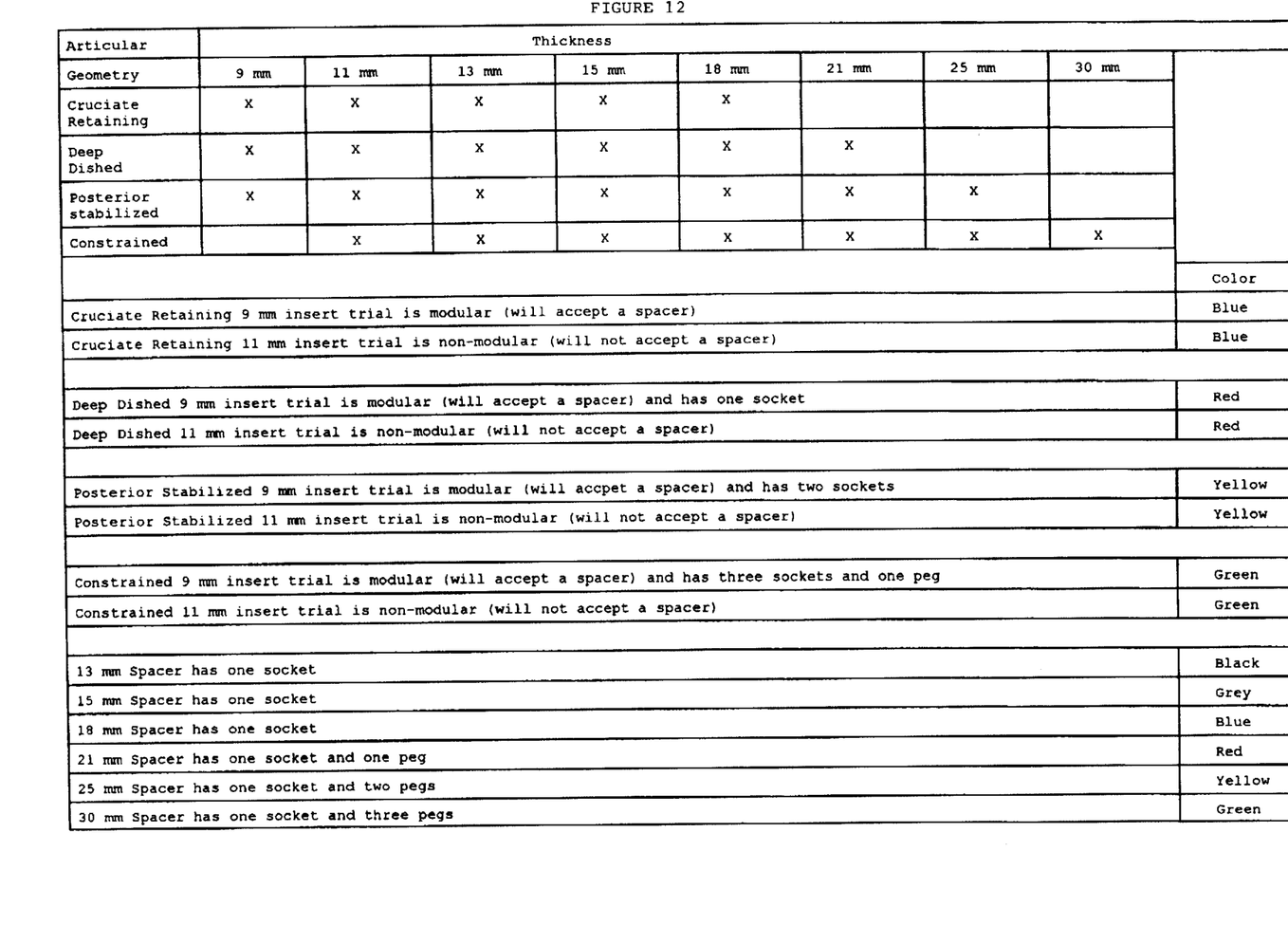
FIG. 12 is a table designating space sizes available for each insert liner of a particular articular geometry.

FIG. 12 is a table that is a designation of spacer sizes available for each insert liner of a particular articular geometry. As shown in FIG. 12, the liner inserts with cruciate retaining articular geometry can have a final thickness (i.e., when combined with a spacer) of between 9 and 18 mm. The liner inserts having a deep dished articular geometry can have a final thickness (i.e., when combined with a spacer) of between 9 and 21 mm. The liner inserts with a posterior stablized articular geometry can have a final thickness when combined with a spacer of between 9 and 25 mm. The liner inserts with a constrained articular geometry can have a final thickness (i.e., insert liner plus a spacer) of between 11 and 30 mm.

Some of the liner inserts are modular in that they will accept a spacer. However, some of the liner inserts are non-modular in that they will not accept a spacer. The following liner inserts are non-modular and will not accept an insert: 11 mm cruciate retaining; 11 mm deep dished; 11 mm posterior stablized; and 11 mm constrained.

The following table lists the parts numbers and parts descriptions as used herein and in the drawings attached hereto.

| PARTS LIST | |
|---|---|
| Part Number | Description |
| 10 | tibial trial insert |
| 11 | top insert |
| 11A | concavity |
| 11B | concavity |
| 11C | raised portion |
| 12 | spacer |
| 13 | rectangular slot |
| 14 | flat surface |
| 15 | flat surface |
| 16 | flat surface |
| 17 | distal surface |
| 18 | locking portion |
| 19 | locking portion |
| 20 | opening |
| 21 | opening |
| 22 | post |
| 23 | post |
| 24 | raised center portion |
| 25 | locking portion |
| 26 | locking portion |
| 27 | rectangular slot |
| 28 | proximal surface |
| 29 | distal surface |
| 30 | proximal tray surface |
| 31 | periphery |
| 32 | periphery |
| 33 | common sidewall |
| 34 | tray periphery |
| 35 | periphery proximal tibia |
| 36 | tibia |
| 37 | articulating surface |
| 38 | articulating surface |
| 39 | socket |
| 40 | articulating surface |
| 41 | socket |
| 42 | socket |
| 43 | projecting portion |
| 44 | projecting portion |
| T | tray |
| S | stem |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A tibial trial prosthesis for attachment to a patient's transversely cut proximal tibia, comprising:

a) a tibial tray having a proximal and a distal surface, the distal surface fitting against a patient's surgically prepared proximal tibia during knee joint replacement surgery;

b) a plastic liner insert that fits the tray with an interlocking connection, the liner having a distal surface and a proximal articulating surface that is receptive of a distal femoral articulating surface, the proximal articulating surface having concavely-shaped portions;

c) a plurality of spacers that can be positioned in between the plastic liner insert and the tibial tray, each having proximal and distal surfaces, at least one of said spacers having connecting portions on each of said proximal and distal surfaces for forming respective connections with the tibial tray and plastic liner;

d) the liner insert having a connecting portion on its distal surface for selectively connecting to the proximal surface of the spacer and alternatively to the proximal surface of the tray; and e) the liner insert and spacers each having a periphery in the form of a sidewall that is an extension generally of the patient's proximal tibia.

2. The tibial trial prosthesis of claim 1 wherein the proximal articulating surface of the liner is a deep dished articular geometry.

3. The tibial trial prosthesis of claim 1 wherein the proximal articulating surface of the liner is a posterior stabilized articular geometry.

4. The tibial trial prosthesis of claim 1 wherein the proximal articulating surface of the liner is a constraining articular geometry.

5. The tibial trial prosthesis of claim 2 wherein there are a plurality of spacers that when attached to the liner insert have a thickness of between 9 mm and 21 mm.

6. The tibial trial prosthesis of claim 3 wherein there are a plurality of spacers that when attached to the liner insert have a thickness of between 9 mm and 25 mm.

7. The tibial trial prosthesis of claim 4 wherein there are a plurality of spacers that when attached to the liner insert have a thickness of between 9 mm and 30 mm.

8. The tibial trial prosthesis of claim 5 wherein spacers between 11 and 18 mm in thickness have no projecting portion on the proximal surface thereof that fits any liner insert.

9. The tibial trial prosthesis of claim 6 wherein spacers between 18 and 21 mm in thickness have a projecting portion on the proximal surface thereof that fits a correspondingly shaped socket on the distal surface of the liner insert.

10. The tibial trial prosthesis of claim 9 wherein spacers between 21 and 25 mm in thickness have a pair of projections on the proximal surface thereof that fit correspondingly placed and shaped sockets on the distal surface of the liner insert.

11. The tibial trial prosthesis of claim 7 wherein spacers between 25 and 30 mm have three projections on the proximal surface thereof that fit correspondingly placed and shaped sockets on the distal surface of the liner insert.

12. The tibial trial insert of claim 2 further comprising a second plastic liner insert that fits the tray, the second plastic liner having a different articular geometry from the first liner insert and wherein some of the spacers and some of the trial inserts have corresponding interlocking portions the trial inserts have corresponding interlocking portions that allow them to be fitted together but disallow attachment to other of the spacers or liners.

13. The tibial trial prosthesis of claim 6 wherein some of the spacers fit some of the liner inserts of one articular geometry but not inserts of other articular geometry.

14. The tibial trial prosthesis of claim 6 wherein some of the spacers have connecting portions that allow attachment to liner inserts of one articular geometry but do not allow attachment to liner inserts of other articular geometry.

15. The tibial trial prosthesis of claim 6 wherein some of the spacers have projecting portions and some of the liner inserts have corresponding socket portions that allow attachment of a selected spacer to certain liner inserts of one articular geometry but do not allow attachment to liner inserts of other articular geometry.

16. The tibial trial prosthesis of claim 15 wherein some of the spacers have projecting portions and some of the liner inserts have corresponding socket portions that allow attachment of a selected spacer to a certain liner insert of a particular selected articular geometry, wherein the projecting portion and socket engage upon assembly, and wherein liner inserts without a corresponding socket do not allow attachment to the liner inserts having said projecting portions.

17. A tibial trial prosthesis for attachment to a patient's transversely cut proximal tibia, comprising:

a) a tibial tray having a proximal and a distal surface, the distal surface fitting against a patient's surgically prepared proximal tibia during knee joint replacement surgery;

b) a plastic liner insert that fits the tray with an interlocking connection, the liner having a distal surface and a proximal articulating surface that is receptive of a distal femoral articulating surface, the proximal articulating surface having concavely-shaped portions;

c) a plurality of spacers that can be positioned in between the plastic liner insert and the tibial tray, each having proximal and distal surfaces, at least one of said spacers having connecting portions on each of said proximal and distal surfaces for forming respective connections with the tibial tray and plastic liner;

d) the liner insert having a connecting portion on its distal surface for selectively connecting to the proximal surface of the spacer and alternatively to the proximal surface of the tray;

e) the liner insert and spacers each having a periphery in the form of a sidewall that is an extension generally of the patient's proximal tibia; and f) wherein the proximal articulating surface of the liner is a cruciate retaining articular geometry.

18. A tibial trial prosthesis for attachment to a patient's transversely cut proximal tibia, comprising:

a) a tibial tray having a proximal and a distal surface, the distal surface fitting against a patient's surgically prepared proximal tibia during knee joint replacement surgery;

b) a plastic liner insert that fits the tray with an interlocking connection, the liner having a distal surface and a proximal articulating surface that is receptive of a distal femoral articulating surface, the proximal articulating surface having concavely-shaped portions;

c) a plurality of spacers that can be positioned in between the plastic liner insert and the tibial tray, each having proximal and distal surfaces, at least one of said spacers having connecting portions on each of said proximal and distal surfaces for forming respective connections with the tibial tray and plastic liner;

d) the liner insert having a connecting portion on its distal surface for selectively connecting to the proximal surface of the spacer and alternatively to the proximal surface of the tray;

e) the liner insert and spacers each having a periphery in the form of a sidewall that is an extension generally of the patient's proximal tibia; and f) wherein there are a plurality of spacers of differing thickness as measured between the proximal and distal surfaces of each spacer, and wherein each trial prosthesis is comprised of an assembly of a tray, a spacer, and a liner.

19. The tibial trial prosthesis of claim 18 wherein at least some of the spacers are thicker than the liner when measured along a line that extends between the proximal and distal surfaces of the liner.

20. A tibial trial prosthesis for attachment to a patient's transversely cut proximal tibia, comprising:
   a) a tibial tray having a proximal and a distal surface, the distal surface fitting against a patient's surgically prepared proximal tibia during knee joint replacement surgery;
   b) a plastic liner insert that fits the tray with an interlocking connection, the liner having a distal surface and a proximal articulating surface that is receptive of a distal femoral articulating surface, the proximal articulating surface having concavely-shaped portions;
   c) a plurality of spacers that can be positioned in between the plastic liner insert and the tibial tray, each having proximal and distal surfaces, at least one of said spacers having connecting portions on each of said proximal and distal surfaces for forming respective connections with the tibial tray and plastic liner;
   d) the liner insert having a connecting portion on its distal surface for selectively connecting to the proximal surface of the spacer and alternatively to the proximal surface of the tray;
   e) the liner insert and spacers each having a periphery in the form of a sidewall that is an extension generally of the patient's proximal tibia; and
   f) wherein there are a plurality of trays and a plurality of spacers of differing thickness that attach to each tray, each spacer thickness being measured between the proximal and distal surfaces of a selected spacer, and wherein at least one of said trial prosthesis is comprised of an assembly of a selected tray and a liner, and at least some of said trial prosthesis for a given tray size are comprised of an assembly of a selected tray, a selected liner and a selected spacer.

21. The tibial trial prosthesis of claim 20 wherein at least some of the spacers are thicker than the liner when measured between the proximal and distal surfaces of the liner.

22. A tibial trial prosthesis for attachment to a patient's transversely cut proximal tibia, comprising:
   a) a tibial tray having a proximal and a distal surface, the distal surface fitting against a patient's surgically prepared proximal tibia during knee joint replacement surgery;
   b) a plastic liner insert that fits the tray with an interlocking connection, the liner having a distal surface and a proximal articulating surface that is receptive of a distal femoral articulating surface, the proximal articulating surface having concavely-shaped portions;
   c) a plurality of spacers that can be positioned in between the plastic liner insert and the tibial tray, each having proximal and distal surfaces, at least one of said spacers having connecting portions on each of said proximal and distal surfaces for forming respective connections with the tibial tray and plastic liner;
   d) the liner insert having a connecting portion on its distal surface for selectively connecting to the proximal surface of the spacer and alternatively to the proximal surface of the tray;
   e) the liner insert and spacers each having a periphery in the form of a sidewall that is an extension generally of the patient's proximal tibia; and
   f) wherein there are a plurality of spacers when attached to the liner insert that have a thickness of between 9 mm and 18 mm.

23. A tibial trial prosthesis for attachment to a patient's transversely cut proximal tibia, comprising:
   a) a tibial tray having a proximal and a distal surface, the distal surface fitting against a patient's surgically prepared proximal tibia during knee joint replacement surgery;
   b) a plastic liner insert that fits the tray with an interlocking connection, the liner having a distal surface and a proximal articulating surface that is receptive of a distal femoral articulating surface, the proximal articulating surface having concavely-shaped portions;
   c) a plurality of spacers that can be positioned in between the plastic liner insert and the tibial tray, each having proximal and distal surfaces, at least one of said spacers having connecting portions on each of said proximal and distal surfaces for forming respective connections with the tibial tray and plastic liner;
   d) the liner insert having a connecting portion on its distal surface for selectively connecting to the proximal surface of the spacer and alternatively to the proximal surface of the tray;
   e) the liner insert and spacers each having a periphery in the form of a sidewall that is an extension generally of the patient's proximal tibia; and
   f) wherein there are a plurality of liner inserts of differing articular geometry.

24. A tibial trial prosthesis for attachment to a patient's transversely cut proximal tibia, comprising:
   a) a tibial tray having a proximal and a distal surface, the distal surface fitting against a patient's surgically prepared proximal tibia during knee joint replacement surgery;
   b) a plastic liner insert that fits the tray with an interlocking connection, the liner having a distal surface and a proximal articulating surface that is receptive of a distal femoral articulating surface, the proximal articulating surface having concavely-shaped portions;
   c) a plurality of spacers that can be positioned in between the plastic liner insert and the tibial tray, each having proximal and distal surfaces, at least one of said spacers having connecting portions on each of said proximal and distal surfaces for forming respective connections with the tibial tray and plastic liner;
   d) the liner insert having a connecting portion on its distal surface for selectively connecting to the proximal surface of the spacer and alternatively to the proximal surface of the tray;
   e) the liner insert and spacers each having a periphery in the form of a sidewall that is an extension generally of the patient's proximal tibia; and
   f) wherein there are multiple liner inserts of differing articular geometries, and there are more spacers than liners in order to reduce space that is necessary to contain the different insert liners and spacers during sterilization.

25. A modular tibial trial prosthesis for attachment to a patient's transversely cut proximal tibia, comprising:
   a) a tibial tray having a proximal and a distal surface, the distal surface fitting against a patient's surgically prepared proximal tibia during knee joint replacement surgery;
   b) a plurality of plastic liner inserts that fits the tray with an interlocking connection, the liner inserts each having a distal surface and a proximal articulating surface that is receptive of a distal femoral articulating surface, the proximal articulating surface having concavely-shaped portions;

c) the concavely-shaped portions of the liner inserts providing different articular geometries for selection by the user;

d) a plurality of spacers of different thicknesses that can be positioned in between a selected one of the plastic liner inserts and the tibial tray, each spacer having proximal and distal surfaces, said spacers having connecting portions on each of said proximal and distal surfaces for forming respective connections with the tibial tray and a selected plastic liner insert;

e) the liner inserts each having a connecting portion on the distal surface thereof for selectively connecting to the proximal surface of the spacer and alternatively to the proximal surface of the tray; and f) the liner inserts and spacers each having a periphery in the form of a sidewall that extends generally perpendicular to the proximal surface of the patient's transversely cut proximal tibia, the periphery of the insert and spacers forming an extension generally to the periphery of the patient's proximal tibia.

26. The tibial trial prosthesis of claim 25 wherein spacers between 18 and 21 mm in thickness have a projecting portion on the proximal surface thereof that fits a correspondingly shaped socket on the distal surface of the liner insert.

27. The tibial trial prosthesis of claim 26 wherein spacers between 21 and 25 mm in thickness have a pair of projections on the proximal surface thereof that fit correspondingly placed and shaped sockets on the distal surface of the liner insert.

28. The tibial trial prosthesis of claim 25 wherein spacers between 25 and 30 mm have three projections on the proximal surface thereof that fit correspondingly placed and shaped sockets on the distal surface of the liner insert.

29. The tibial trial insert of claim 25 further comprising a second plastic liner insert that fits the tray, the second plastic liner having a different articular geometry from the first liner insert and wherein some of the spacers and some of the trial inserts have corresponding interlocking portions that allow them to be fitted together but disallow attachment to other of the spacers or liners.

30. The tibial trial insert of claim 25 wherein there are multiple liner inserts of differing articular geometries, and there are more spacers than liners in order to reduce space that is necessary to contain the different insert liners and spacers during sterilization.

31. The modular tibial trial prosthesis of claim 25 wherein corresponding inserts of the same articular geometry match in color those spacers that fit within the maximum overall designed thickness for said inserts upon assembly with said color match spacer.

* * * * *